(12) United States Patent
Verseck et al.

(10) Patent No.: US 7,070,963 B2
(45) Date of Patent: Jul. 4, 2006

(54) AMIDASE FROM VARIOVORAX

(75) Inventors: Stefan Verseck, Hanau (DE);
Karlheinz Drauz, Freigericht (DE);
Andreas Bommarius, Atlanta, GA (US); Maria-Regina Kula, Niederzier (DE); Lutz Krieg, Juelich (DE); Heike Slusarczyk, Uebach-Palenberg (DE); Marion Ansorge-Schumacher, Aachen (DE)

(73) Assignee: Degussa AG, Duesseldorf (DE)

( * ) Notice: Subject to any disclaimer, the term of this patent is extended or adjusted under 35 U.S.C. 154(b) by 537 days.

(21) Appl. No.: 10/309,294

(22) Filed: Dec. 4, 2002

(65) Prior Publication Data

US 2003/0186423 A1    Oct. 2, 2003

(30) Foreign Application Priority Data

Dec. 6, 2001    (DE) ................... 101 60 066

(51) Int. Cl.
*C12P 13/04*    (2006.01)
*C12P 7/62*    (2006.01)
*C12N 9/80*    (2006.01)

(52) U.S. Cl. ............... 435/106; 435/135; 435/228
(58) Field of Classification Search ............ 435/228, 435/135, 106
See application file for complete search history.

(56) References Cited

FOREIGN PATENT DOCUMENTS

| EP | 0 334 358 | 9/1989 |
|----|-----------|--------|
| WO | WO 97/12964 | 1/1997 |

OTHER PUBLICATIONS

Krieg, L, et al. (2002) Adv. Synth. Catal. 344(9), 965-973.*
T. Hayashi, et al., Journal of Fermentation and Bioengineering, vol. 83, No. 2, pp. 139-145, XP-009009228, "Characterization and Cloning of an Enantioselective Amidase From *Comamonas acidovorans* KPO-2771-4", 1997 (with corr. Database EMBL 'Online!', AN AAT47765,).
Database EMBL 'Online', AN AAT47765, pp. 1-2, XP-002237979, "*Comamonas acidovorans* Derived Amidase Gene", May 2, 1997.
A. Ozaki et al., Bioscience Biotechnology and Biochemistry, vol. 57, No. 3, pp. 520-521, XP-009009243, "A D-Amidase Constitutive Mutant From *Arthrobacter* sp. NJ-26", 1993.
J. R. Leadbetter, et al., Journal of Bacteriology, vol. 182, No. 24, pp. 6921-6926, XP-002208346, "Metabolism of Acyl-Homoserine Lactone Quorum-Sensing Signals by *Variovorax paradoxus*", Dec. 2000.

* cited by examiner

Primary Examiner—Charles L. Patterson, Jr.
(74) Attorney, Agent, or Firm—Oblon, Spivak, McClelland, Maier & Neustadt, P.C.

(57) ABSTRACT

The present invention relates to an amidase enzyme, nucleic acids encoding the amidase, as well as methods of employing the nucleic acids and/or amidase to produce, for example, enantiomericallyenriched compounds such as D-amino acids.

12 Claims, 4 Drawing Sheets

AMIDASE FROM VARIOVORAX

BACKGROUND OF THE INVENTION

1. Field of the Invention

The present invention relates to an amidase enzyme, nucleic acids encoding the amidase, as well as methods of employing the nucleic acids and/or amidase to produce, for example, enantiomerically enriched compounds such as D-amino acids.

2. Discussion of the Background

Amidases or amidohydrolases are classified according to the E.C. system into two sub-classes, E.C. 3.5.1.1 to 3.5.1.77 and E.C. 3.5.2.1 to 3.5.2.14. Representatives of the first sub-class are e.g. asparaginase (E.C. 3.5.1.1), urease (E.C. 3.5.1.5) and the acylamide amidohydrolase considered in more detail here (E.C. 3.5.1.4).

The acylamide amidohydrolase is widespread within microorganisms and occurs, inter alia, in species such as *Corynebacteria*, *Pseudomonas*, *Bacilli*, *Brevibacteria*, *Rhodococci* and *Alcaligenes*. These are usually inducible enzymes, the specificity of which varies greatly from organism to organism (Maestracci, M.; Bui, K.; Thiéry, A.; Arnaud, A.; Galzy, P. (1988), The Amidases from a *Brevibacterium* Strain: Study and Applications, Adv. Biochem. Eng. 36, 69–115).

The enzymes from *Mycobacterium neoaurum* ATCC 25795 (Hermes, H. F. M.; Tandler, R. F.; Sonke, T.; Dijkhuizen, L.; Meijer, E. M. (1994), Purification and Characterization of an L-Amino Amidase from *Mycobacterium neoaurum* ATCC 25795, Appl. Environ. Microbiol. 60, 153–159) and *Pseudomonas putida* ATCC 12633 (Hermes, H. F. M.; Sonke, T.; Peters, P. J. H.; van Balken, J, A. M.; Kamphuis, J.; Dijkhuizen, L.; Meijer, E. M. (1993), Purification and Characterization of an L-Aminopeptidase from *Pseudomonas putida* ATCC 12633, Appl. Environ. Microbiol. 59, 4330–4334) are of particular industrial importance for the hydrolysis of L-amino acid amides. Both enzymes show a relatively high affinity for N-branched amino acid amides or dipeptides and are therefore classified as aminopeptidases (E.C. 3.4.). The L-aminopeptidase from *Pseudomonas putida* ATCC 12633 is employed for stereospecific cleavage of a D,L-phenylglycinamide mixture into D-phenylglycinamide and L-phenylglycine. A process developed by the DSM utilizes whole cells of *Pseudomonas putida* for the preparation of pure D- and L-amino acids from D,L-amino acid amides (Kamphuis, J.; Boesten, W. H. J.; Broxterman, Q. B.; Hermes, H. F. M.; Balkan van, J. A. M.; Meijer, E. M.; Shoemaker, H. E. (1990), New developments in the chemo-enzymatic production of amino acids, Adv. Biochem. Eng. Biotechnol. 42, 133–186).

A process for the preparation of L-amino acids and amino acid amides from D,L-α-aminonitriles is described in Klages, U.; Weber, A. (1988), Verfahren zur Herstellung von L-Aminosäuren und Aminosäureamiden, DE 3 816 063 A1; WO 8 910 969). In this biotransformation with whole cells, D,L-aminonitriles are first hydrolysed to D,L-amino acid amides with *Acinetobacter calcoaceticus* DSM 3875. Complete conversion into the L-amino acid is in principle possible with an L-amino acid amidase and an amino acid amide racemase in *Arthrobacter* sp. ATCC 31652 or *Corynebacterium* sp. ATCC 31662.

As a result of the discovery of amino acid amide racemases in *Pseudomonas putida* and *Rhodococcus* sp., a process for the racemization of amino acid amides and hydrolysis by an L- or D-amidase to give the corresponding amino acid is described in Godtfredsen, S. E.; Clausen, K.; Ingvorsen, K.; Hermes, H. F.; Van Balken, J. A.; Meijer, E. M. (1989), EP 0 307 023; WO 8 901 525. A D-amidase activity has been described here in *Pseudomonas putida* NCIB 40042 and *Rhodococcus* sp. NCIB 40041.

The discovery of a further amino acid racemase in *Klebsiella oxytoca* is described by Hermes, H. F. M.; Peeters, W. P.; Peters, P. J. (1990), EP 0 383 403.

Amidases with a D-specificity to amino acid amides have been described in *Comamonas acidovorans* KPO-2771–4 (Hayashi, T.; Yamamoto, K.; Matsuo, A.; Otsubo, K.; Muramatsu, S.; Matsuda, A.; Komatsu, K.-I. (1997), Characterization and Cloning of an Enantioselective Amidase from *Comamonas acidovorans* KPO-2771–4, J. Ferment. Bioeng. 83, 139–145) and in two strains of *Ochrobactrum anthropi*, SCRC C1-38 (Asano, Y.; Kato, Y.; Yamada, A.; Kondo, K. (1992) Structural Similarity of D-Aminopeptidase to Carboxypeptidase DD and β-Lactamases, Biochem. 31, 2316–2328; Asano, Y.; Nakazawa, A.; Kato, Y.; Kondo, K. (1989), Properties of a Novel D-Stereospecific Aminopeptidase from *Ochrobactrum anthropi*, J. Biol. Chem. 264, 14233–14239) and SCRC-SV3 (Komeda, H. and Asano, Y. (2000), Gene cloning, nucleotide sequencing, and purification and characterisation of the D-stereospecific amino-acid amidase from *Ochrobactrum anthropi* SV3, Eur. J. Biochem. 267, 2028–2035; Asano, Y.; Mori, T.; Hanamoto, S.; Kato, Y.; Nakazawa, A. (1989), A New D-Stereospecific Amino Acid Amidase From *Ochrobactrum anthropi*, Biochem. Biophys. Res. Commun. 162, 470–474).

Nevertheless, there is still a need for D-amidases, especially since their substrate spectra are not covered 100% and for the preparation of poorly convertible substrates on an industrial scale under economically advantageous conditions.

SUMMARY OF THE INVENTION

Therefore, one object of the present invention is to provide new D-amidases, and in particular, the amidases with the amino acid sequence of SEQ ID NO:2 as well as those enzymes that are at least 80% identical to SEQ ID NO:2 and which have D-amidase activity.

Another object of the present invention is those polynucleotides, which encode for the amidase enzymes. In one embodiment, the polynucleotide has the sequence shown in SEQ ID NO:1. In another embodiment, the polynucleotide is at least 80% identical to SEQ ID NO:1 and/or hybridizes under stringent conditions to the complement of SEQ ID NO:1.

Another object of the present invention is a method for preparing and identifying amidase enzymes with improved activity and/or improved substrate selectivity. This method involves mutagenizing an amidase encoding polynucleotide and then screening the proteins expressed from the mutagenized polynucleotide for those improved properties.

Another object of the present invention is to utilize those amidase enzymes to prepare enantiomerically enriched compounds, such as amino acids.

In another object of the present invention, the amidase enzymes are utilized to prepare carboxylic acid compounds from the corresponding carboxylic acid amides.

DETAILED DESCRIPTION OF THE INVENTION

Figure 1:
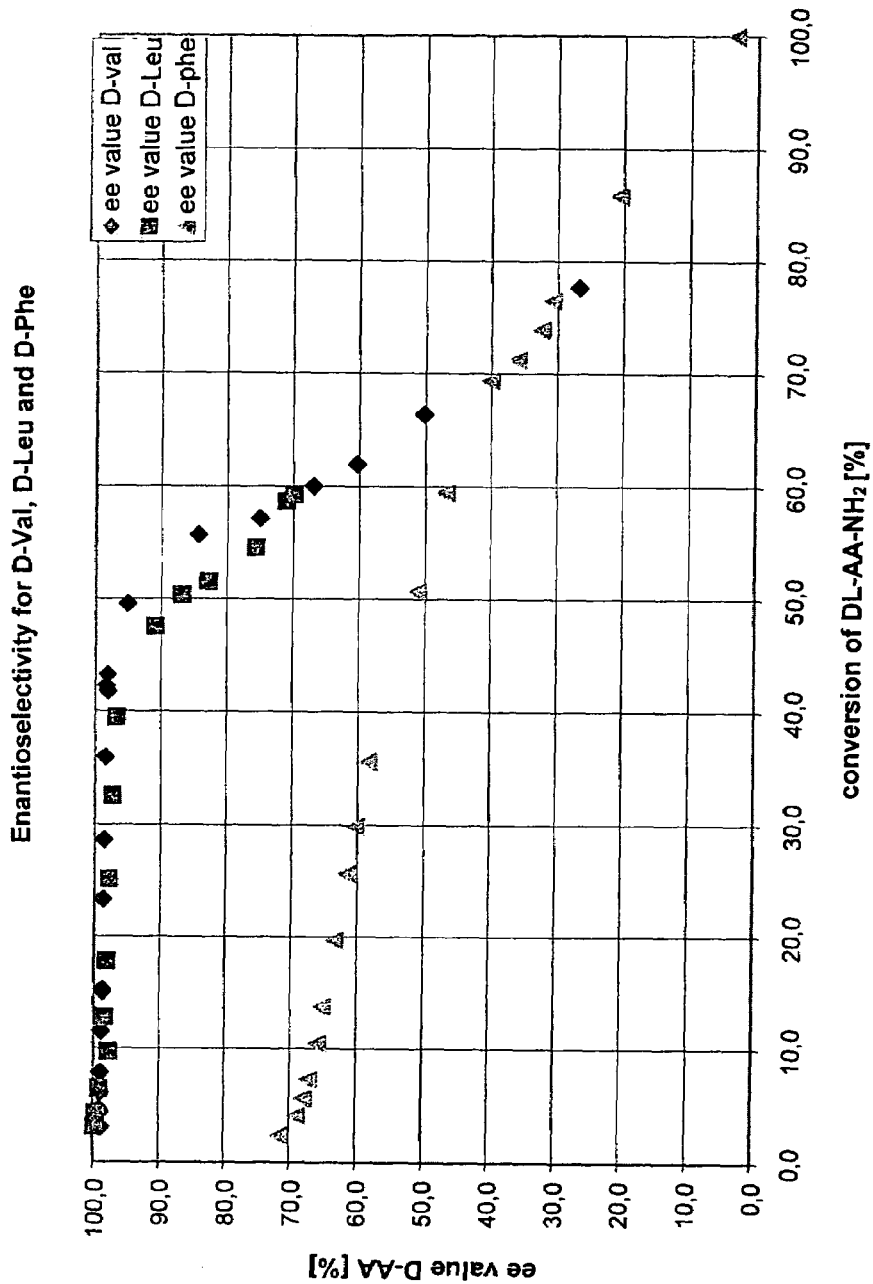
FIG. 1 shows the enantioselectivity for D-Val, D-Leu and D-Phe as a function of the conversion.

In the context of the invention, optically enriched (enantiomerically enriched, enantiomer-enriched) compounds is understood as meaning the presence of one optical antipode as a mixture with the other in >50 mol %.

The D-amidase according to the invention is capable of catalysing the hydrolysis of a broad spectrum of carboxylic acid amides into the corresponding carboxylic acids. In this reaction, racemic mixtures of e.g. amino acid amides are converted in some cases strictly D-selectively. With the present invention it is possible, surprisingly, to obtain enantiomerically enriched D-tert-leucine from racemic tert-leucinamide in a turn-over frequency which is adequate for an industrial process.

The D-amidase of the present invention can be isolated from a Variovorax organism, such as for, example, *Variovorax paradoxus*. In one embodiment, the *Variovorax paradoxus* is 19–3 DSM 14468. The amino acid sequene of the *Variovorax paradoxus* 19-3 DSM 14468 D-amidase is shown in SEQ ID NO:2.

Another embodiment of the invention is the microorganism *Variovorax paradoxus* 19-3 deposited in accordance with the Budapest Treaty at the DSMZ on Aug. 22, 2001 and assigned the accession number DSM 14468.

Notwithstanding the ease of culturing Variovorax strains and isolating the enzyme by, for example, chromatographic methods, nucleic acids which code for a D-amidase can be employed to facilitate the production of the enzyme. Using host cells that are transformed with the coding nucleic acids, it is possible to obtain the enzymes in high yields from fast-growing host organisms. These nucleic acid sequences can also be used for producing improved mutants. Therefore, the present invention also embodies the polynucleotides which encode the D-amidase. The term polynucleotide includes, nucleic acids such as single-stranded or double-stranded DNA and also RNA or mixtures thereof. In one embodiment, the polynucleotide which encodes the enzyme with the amino acid sequence in SEQ ID NO:2 is SEQ ID NO:1. The invention also includes nucleic acids which hybridize under stringent conditions with the single-stranded nucleic acids according to the invention or single-stranded nucleic acids complementary thereto. One embodiment of such a hybridizing sequence is shown as SEQ ID NO:5.

The expression "under stringent conditions" is understood herein as described by Sambrook, J.; Fritsch, E. F. and Maniatis, T. (1989), Molecular cloning: a laboratory manual, 2nd ed., Cold Spring Harbor Laboratory Press, New York; and includes the conditions where the hybridization is detected after the hybridization reaction is washed for one hour with 1×SSC (150 mM sodium chloride, 15 mM sodium citrate, pH 7.0) and 0.1% SDS (sodium dodecyl sulfate) at 50° C., preferably at 55° C., more preferably at 62° C. and most preferably at 68° C. and more preferably for 1 hour with 0.2×SSC and 0.1% SDS at 50° C., more preferably at 55° C., even more preferably at 62° C. and most preferably at 68° C.

In another embodiment, the invention provides those proteins and polynucleotide sequence, which are greater than 80% homologous, including greater than 85%, 90%, 91%, 92%, 93% 94%, 95% 96%, 97%, 98% or 99%, to SEQ ID NO:1 or SEQ ID NO:2. For use of the enzymes for the purposes described in this application, the enzymes themselves or those encoded therein should have at least some amidase activity as can be measured according to the assays described herein. The amount of activity would be at least 10%, at least 20%, at least 30%, at least 40%, at least 50%, at least 60%, at least 70%, at least 80% or at least 90% of the amidase activity relative to the activity of the protein having the amino acid sequence SEQ ID NO:2.

The expression "homology" (or identity) as used herein can be defined by the equation $H\ (\%) = [1 - V/X] \times 100$, wherein H denotes homology, X is the total number of nucleobases/amino acids of the comparison sequence and V is the number of different nucleobases/amino acids of the sequence in question with respect to the comparison sequence. In all cases, the term nucleic acids which code for amino acid sequences includes all sequences which are possible in light of the degeneration of the genetic code.

The polynucleotides described herein may also be constructed into one or more vectors. Possible plasmids or vectors are in principle all the embodiments available to the expert for this purpose. Such plasmids and vectors can be obtained e.g. from Studier and colleagues (Studier, W. F.; Rosenberg A. H.; Dunn J. J.; Dubendroff J. W.; (1990), Use of the T7 RNA polymerase to direct expression of cloned genes, Methods Enzymol. 185, 61–89) or the brochures of Novagen, Promega, New England Biolabs, Clontech or Gibco BRL. Further preferred plasmids and vectors can be found in: Glover, D. M. (1985), DNA cloning: A Practical Approach, vol. I–III, IRL Press Ltd., Oxford; Rodriguez, R. L. and Denhardt, D. T (eds) (1988), Vectors: a survey of molecular cloning vectors and their uses, 179–204, Butterworth, Stoneham; Goeddel, D. V. (1990), Systems for heterologous gene expression, Methods Enzymol. 185, 3–7; Sambrook, J.; Fritsch, E. F. and Maniatis, T. (1989), Molecular cloning: a laboratory manual, $2^{nd}$ ed., Cold Spring Harbor Laboratory Press, New York. Plasmids with which the gene construct containing the nucleic acid according to the invention can be cloned in a very preferred manner into the host organism are: pUC18 (Roche Biochemicals), pKK-177-3H (Roche Biochemicals), pBTac2 (Roche Biochemicals), pKK-233-3 (Stratagene) or pET (Novagen).

In another embodiment of the invention, the polynucleotides encoding the amidase enzymes can be provided in one or more microorganims, such as by transformation using common recombinant molecular biology techniques. In one embodiment, the polynucleotides are first constructed in one or more of the vectors described above and then the vector carrying the polynucleotides encoding amidase are transferred into the microorganisms. The microorganism into which the nucleic acids are cloned is used for increasing and obtaining a sufficient amount of the recombinant enzyme. The processes for this are well-known to the expert (Sambrook, J.; Fritsch, E. F. and Maniatis, T. (1989), Molecular cloning: a laboratory manual, 2nd ed., Cold Spring Harbor Laboratory Press, New York). Microorganisms which can be used are in principle all the organisms possible to the expert for this purpose, such as e.g. yeasts, such as *Hansenula polymorpha, Pichia* sp. and *Saccharomyces cerevisiae*, prokaryotes, such as *E. coli* and *Bacillus subtilis* or eukaryotes, such as mammalian cells and insect cells. *E. coli* strains are preferably to be used for this purpose. The following are very particularly preferred: *E. coli* XL1 Blue, NM 522, JM101, JM109, JM105, RR1, DH5α, TOP 10⁻ or HB 101. Plasmids with which the gene construct containing the nucleic acid according to the invention is preferably cloned into the host organism are mentioned above.

Another aspect of the invention relates to primers for the preparation of the gene sequences according to the invention by means of all types of PCR. These also include. the sense and antisense primers which code for the corresponding amino acid sequences, or complementary DNA sequences. Suitable primers can in principle be obtained by processes known to the expert. The discovery of the primers according to the invention is undertaken by comparison with known DNA sequences or by translating the amino acid sequences under consideration into the preferred codon of the organism in question (e.g. for Streptomyces: Wright F. and Bibb M. J. (1992), Codon usage in the G+C-rich Streptomyces genome, Gene 113, 55–65). Common features in the amino acid sequence of proteins of so-called super-families are also of benefit for this (Firestine, S. M.; Nixon, A. E.; Benkovic, S. J. (1996), Threading your way to protein function, Chem. Biol. 3, 779–783). Further information in this respect can be found in Gait, M. J. (1984), Oligonucleotide synthesis: a practical approach, IRL Press Ltd., Oxford; Innis, M. A.; Gelfound, D. H.; Sninsky, J. J. and White, T. J. (1990), PCR Protocols: A guide to methods and applications, Academic Press Inc., San Diego.

Preferred primers include:

```
AAH-N1:                                    (SEQ ID NO:3)
5'GTS GGC CGS CGS ATC CAG CAG AAG GA 3'

AAH-C1:                                    (SEQ TD NO:4)
5'GGG ATS CGG ATC GAG CCG CCS GTS TC 3'
```

S represents G+C in the sequence of AAH-N1 and AAH-C1 (IUB group code for identification of redundancies).

mutagenesis, in vitro recombination methods and site-directed mutagenesis (Eigen, M. and Gardiner, W. (1984), Evolutionary molecular engineering based on RNA replication, Pure Appl. Chem. 56, 967–978; Chen, K. and Arnold, F. (1991), Enzyme engineering for nonaqueous solvents: random mutagenesis to enhance activity of subtilisin E in polar organic media. Bio/Technology 9, 1073–1077; Horwitz, M. and Loeb, L. (1986), Promoters Selected From Random DNA-Sequences, Proc Natl Acad Sci USA 83, 7405–7409; Dube, D. and L. Loeb (1989), Mutants Generated By The Insertion Of Random Oligonucleotides Into The Active-Site Of The Beta-Lactamase Gene, Biochemistry 28, 5703–5707; Stemmer, P. C. (1994), Rapid evolution of a protein in vitro by DNA shuffling, Nature 370, 389–391 and Stemmer, P. C. (1994), DNA shuffling by random fragmentation and reassembly: In vitro recombination for molecular evolution. Proc Natl Acad Sci USA 91, 10747–10751).

These new nucleic acid sequences obtained by these methods can be cloned into a host organism by the methods described herein whereby the enzymes are expressed; detected with suitable screening methods; and then isolated. Suitable methods for the detection are in principle all the possible detection reactions for ammonia and ammonium ions, such as Nessler's reagent (Vogel, A. I. (1989), Vogel's textbook of quantitative chemical analysis, John Wiley & Sons, Inc., 5th ed., 679–698, New York), the indophenol reaction, also called Berthelot's reaction (Wagner, R.,

```
AAH-GW-F1:    5' GCG TCA CGC CGC CGG TCA ATC CGT GGA A 3'      (SEQ ID NO:6)

AAH-GW-F2:    5' GGC GCA CTG GTC GGG TGC CTC GTC GA 3'         (SEQ ID NO:7)

AAH-GW-R1:    5' CAG GGC GTG TTC GGC CAT CAC GAT CAC ATA 3'    (SEQ ID NO:8)

AAH-GW-R2:    5' CTC TTG AGC GCG CCG TCG ACC TTC TCG A 3'      (SEQ ID NO:9)

AAH-K-N2:     5' CTG GTC ATC AAG CGC GGC CAG ATC GGC 3'        (SEQ ID NO:10)

AAH-K-C2:     5' GAT CGG CCG ACA GCC GAT TGG CCA GC 3'         (SEQ ID NO:11)

AAH-N-EcoRI:  5' CCG GAA TTC ATG AGC AAC GAA CTG CAT TAC CT 3' (SEQ ID NO:12)

AAH-C-HindIII: 5' ATC CCA AGC TTT TAC AGC ACC GGA TGC CG 3'    (SEQ ID NO:13)
```

In another embodiment, the present invention relates to a process for the preparation of improved rec-D-amidases and rec-D-amidases obtained in this manner or nucleic acids which code these, wherein, starting from the nucleic acids according to the invention which code for a D-amidase according to the invention, a) the nucleic acids are subjected to a mutagenesis,
b) the nucleic acids obtained from a) are cloned into a suitable vector and this is transferred into a suitable expression system, and
c) the proteins of improved activity and/or selectivity formed are detected and isolated.

Improved rec-enzymes are understood to mean those which have a modified substrate spectrum and are more active and/or selective or more stable under the reaction conditions used relative to the unmodified enzyme. In one embodiment, the rec-enzyme would exhibit at least a 5% increase in activity and/or selectivity.

This process can be carried out once or any desired number of times in succession. This and similar methods for improving the activity of the amidase enzymes is known in the art. Likewise, methods of mutagenesis are known and include, for example, saturation mutagenesis, random (1969), Neue Aspekte zur Stickstoffanalytik in der Wasserchemie, Vom Wasser, VCH-Verlag, vol. 36, 263–318, Weinheim), in particular enzymatic determination by means of glutamate dehydrogenase (Bergmeyer, H. U., and Beutler, H.-O. (1985), Ammonia, in: Methods of Enzymatic Analysis, VCH-Verlag, 3rd edition, vol. 8: 454–461, Weinheim) and also detection with ammonium-sensitive electrodes. HPLC methods are furthermore used for detection of amino acids, such as e.g. a derivative method based on o-pthaldialdehyde and N-isobutyryl-cysteine for enantiomer separation of amino acids (Brückner, H., Wittner R., and Godel H. (1991), Fully automated high-performance liquid chromatographic separation of DL-amino acids derivatized with o-Phthaldialdehyde together with N-isopropyl-cysteine. Application to food samples, Anal. Biochem. 144, 204–206).

The present invention also concerns the use of the D-amidases according to the invention for preparing carboxylic acids. In another embodiment, the D-amidases are used to prepare chiral enantiomerically enriched organic compounds, such as amino acids. In another embodiment, the D-amidases used for these methods are the D-amidases that have been improved according the methods described hereinabove.

In one embodiment, the nucleic acids, which encode the amidase, preferably the D-amidase, of the present invention, can be used to prepare a whole cell catalyst. In one embodiment, the whole cell catalyst contains a D-amidase from *Variovorax*, such as from *Variovorax paradoxus*, preferably *Variovorax paradoxus* DSM 14468. These whole cell catalysts can also include one or more cloned genes for a nitrile hydratase, an α-aminonitrile racemase, a cyanohydrin racemase, an α-hydroxycarboxylic acid racemase, and an (α- or β-)amino acid amide racemase (Hermes, H. F. M.; Peeters, W. P.; Peters, P. J. (1990), EP 0 383 403; and WO 8 901 525; Wilms, L.; Bartsch, K. (1995), EP 0 690 133; Klages, U.; Weber, A (1989), WO 8 910 969).

For use, the enzyme in question can be used in the free form as homogeneously purified compounds or as an enzyme prepared by a recombinant method. The enzyme can furthermore also be employed as a constituent of an intact guest organism or in combination with the broken-down cell mass of the host organism, which has been purified to any desired extent. The use of the enzymes in immobilized form is also possible (Sharma B. P.; Bailey L. F. and Messing R. A. (1982), Immobilisierte Biomaterialiern—Techniken und Anwendungen, Angew. Chem. 94, 836–852). The immobilization is advantageously carried out by lyophilization (Paradkar, V. M.; Dordick, J. S. (1994), Aqueous-Like Activity of α-Chymotrypsin Dissolved in Nearly Anhydrous Organic Solvents, J. Am. Chem. Soc. 116, 5009–5010; Mori, T.; Okahata, Y. (1997), A variety of lipi-coated glycoside hydrolases as effective glycosyl transfer catalysts in homogeneous organic solvents, Tetrahedron Lett. 38, 1971–1974; Otamiri, M.; Adlercreutz, P.; Matthiasson, B. (1992), Complex formation between chymotrypsin and ethyl cellulose as a means to solubilize the enzyme in active form in toluene, Biocatalysis 6, 291–305). Lyophilization in the presence of surface-active substances, such as Aerosol OT or polyvinylpyrrolidone or polyethylene glycol (PEG) or Brij 52 (diethylene glycol monocetyl ether) (Kamiya, N.; Okazaki, S.-Y.; Goto, M. (1997), Surfactant-horseradish peroxidase complex catalytically active in anhydrous benzene, Biotechnol. Tech. 11, 375–378), is very particularly preferred. The use as CLECs is also conceivable (St. Clair, N.; Wang, Y.-F.; Margolin, A. L. (2000), Cofactor-bound cross-linked enzyme crystals (CLEC) of alcohol dehydrogenase, Angew. Chem. Int. Ed. 39, 380–383).

The production of such whole cell catalysts is described in, for example, Farwick, M.; London, M.; Dohmen, J.; Dahlems, U.; Gellissen, G.; Strasser, A. W.; DE19920712. The advantage of such whole cell catalysts is the simultaneous expression of both enzymes systems, which means that only one rec-organism has to be used for the reaction. To match the expression of the enzymes in respect of their rates of conversion, the correspondingly coding nucleic acid fragments can be accommodated on different plasmids with different numbers of copies and/or promoters of different potency can be used for an expression of the genes of different intensity. In such matched enzyme systems, advantageously no accumulation of an intermediate compound which may have an inhibiting effect occurs, and the reaction in question can proceed at an optimum overall rate, for example, as described in Gellissen, G.; Piontek, M.; Dahlems, U.; Jenzelewski, V.; Gavagan, J. W.; DiCosimo, R.; Anton, D. L.; Janowicz, Z. A. (1996), Recombinant Hansenula polymorpha as a biocatalyst. Coexpression of the spinach glycollate oxidase (GO) and the *S. cerevisiae* catalase T (CTT1) gene, Appl. Microbiol. Biotechnol. 46, 46–54; Farwick, M.; London, M.; Dohmen, J.; Dahlems, U.; Gellissen, G.; Strasser, A. W.; DE19920712.

The nucleic acids according to the invention can be employed for preparing rec-D-amidases. Using common recombinant techniques, organisms which are capable of providing the enzyme in question in an amount sufficient for an industrial process can be obtained. The preparation of the rec-enzymes according to the invention is carried out by genetic engineering processes such as those described in Sambrook, J.; Fritsch, E. F. and Maniatis, T. (1989), Molecular cloning: a laboratory manual, 2nd ed., Cold Spring Harbor Laboratory Press, New York; Balbas, P. and Bolivar, F. (1990), Design and construction of expression plasmid vectors in *E. coli*, Methods Enzymol. 185, 14–37; Rodriguez, R. L. and Denhardt, D. T (eds) (1988), Vectors: a survey of molecular cloning vectors and their uses, 205–225, Butterworth, Stoneham. With respect to general procedures such as PCR, cloning, expression etc., the following references are cited: Universal GenomeWalker™ Kit User Manual, Clontech, 3/2000 and literature cited therein; Triglia T.; Peterson, M. G. and Kemp, D. J. (1988), A procedure for in vitro amplification of DNA segments that lie outside the boundaries of known sequences, Nucleic Acids Res. 16, 8186; Sambrook, J.; Fritsch, E. F. and Maniatis, T. (1989), Molecular cloning: a laboratory manual, 2nd ed., Cold Spring Harbor Laboratory Press, New York; Rodriguez, R. L. and Denhardt, D. T (eds) (1988), Vectors: a survey of molecular cloning vectors and their uses, Butterworth, Stoneham.

The D-amidase from *Variovorax paradoxus* is classified according to the E.C. system as an acylamide amidohydrolase (E.C. 3.5.1.4). The complete gene sequence of the D-amidase from *Variovorax paradoxus* is shown in SEQ ID NO:1. A gene section of the D-amidase was obtained from *Variovorax paradoxus* by a PCR reaction with genomic DNA. It was possible to obtain a primer, AAH-N1 (SEQ ID NO:3), from the N-terminus of the amino acid sequence determined. The second primer, AAH-C1 (SEQ ID NO; 4) was derived from the consensus region on the basis of the sequence similarity of the N-terminus with representatives of the so-called amidase family. Using these two primers, a fragment of the D-amidase gene 509 bp in size, which can be employed in principle as a gene probe, was amplified by means of the PCR technique. Its sequence of base pairs is shown in SEQ ID NO:5.

With the aid of this fragment, further gene-specific primers which were required for the method of the Universal GenomeWalker™-Kit (Universal GenomeWalker™ Kit User Manual, Clontech, 3/2000 and literature cited therein) of Clontech for discovering the entire gene were constructed (SEQ ID NOS:6–9). With this method, genomic DNA from *Variovorax paradoxus* was first cleaved with EcoRV, PvuII, ScaI and StuI. The batches with the DNA fragments obtained were ligated with the GenomeWalker™ Adapter included, for which two primers exist. With these batches as templates, a PCR reaction was carried out in both directions with the aid of one of the gene-specific primers listed, AAH-GW-F1 (SEQ ID NO:6) or AAH-GW-R1 (SEQ ID NO:8) and an adapter primer. A nested PCR reaction (Universal GenomeWalker™ Kit User Manual, Clontech, 3/2000 and literature cited therein) with the primers AAH-GW-F2 (SEQ ID NO:7) or AAH-GW-R2 (SEQ ID NO:8) and an adapter primer should prevent the formation of non-specific PCR products. The complete gene sequence of the D-amidase was accessible with the PCR fragments of up to 3,500 bp (downstream) and 1,800 bp (upstream) obtained.

For further working and for checking of the gene sequence, the entire D-amidase gene with 92 bp before the start codon and 80 bp after the stop codon was amplified, starting from genomic DNA and the primers SEQ ID NOS: 10 and 11; in three parallel batches with two different DNA polymerases with proofreading (VentR®, New England Biolabs and Herculase®, Stratagene). The PCR products obtained were subjected to blunt-end ligation into the vector pUC18 and transformed in *E. coli* XL1 Blue. Starting from plasmid DNA, the D-amidase sequence (SEQ ID NO:1) could thus be secured and checked (Sequiserve, Vaterstetten, Germany).

For the expression of the D-amidase, an EcoRI cleavage site was introduced at the 5' end and a HindIII cleavage site at the 3' end by a PCR reaction (SEQ ID NOS:12 and 13) and the PCR product was ligated into the pBTAC vector and transformed in *E. coli* JM 101. In a first expression experiment, it was possible to determine a specific activity of between 80 and 210 mU/mg for DL-Tle-$NH_2$ in the crude extract. By comparison with the specific activity in *Variovorax paradoxus* of between 20 and 30 mU/mg in the crude extract, it was possible to achieve a significant over-expression. An analysis of the soluble and insoluble fractions of the crude extracts by SDS-PAGE showed that a large portion of the D-amidase expressed is present in the cell pellet in insoluble form, so-called inclusion bodies.

The amidase is purified in three chromatography steps, usually only a very low content of foreign protein still being present after the 2nd step.
1. Ion exchange chromatography: Q-Sepharose FF (Pharmacia)
2. Hydrophobic interaction chromatography: Butyl-Sepharose 4 FF (Pharmacia)
3. Gel filtration: Superdex 200 PG (Pharmacia)

A yield of 88% can be calculated for the first two purification steps, a specific activity of 0.68 U/mg for DL-Tle-$NH_2$ as the substrate being present. For the homogeneously purified D-amidase from *Variovorax paradoxus*, a specific activity of 1.4 U/mg for DL-Tle-$NH_2$ resulted.

The suitability of the amidase was demonstrated in the following experiments:

1. Acid Amides:

The activity was measured by determination of the ammonium ions with glutamate dehydrogenase (Bergmeyer, H. U., and Beutler, H.-O. (1985), Ammonia. In: Methods of Enzymatic Analysis. VCH-Verlag, 3rd edition, vol. 8: 454–461, Weinheim). The enzyme used was a partly purified D-amidase after the 2nd chromatography step with a specific activity of 0.51 U/mg. The substrates were employed in the enzyme test at 40 mM, except for succinic acid diamide and adipic acid diamide, each at 10 mM, and benzylamide at 20 mM. Since the activities were determined only at in each case one substrate concentration, relative activities are stated.

TABLE 1

Relative enzyme activities for various acid amides with respect to DL-Tle-$NH_2$

| Substrate | Relative act. [U/mg] | Activity with respect to Tle-$NH_2$ |
|---|---|---|
| DL-Tle-$NH_2$ | 0.51 | 1 |
| Formamide | 0.061 | 0.13 |
| Acetamide | 2.1 | 4.0 |
| Propionamide | 12 | 26 |

TABLE 1-continued

Relative enzyme activities for various acid amides with respect to DL-Tle-$NH_2$

| Substrate | Relative act. [U/mg] | Activity with respect to Tle-$NH_2$ |
|---|---|---|
| Butyramide | 17 | 37 |
| Isobutyramide | 15 | 33 |
| Valeric acid amide | 16 | 36 |
| Acetoacetamide | 58 | 130 |
| Malonic acid diamide | 1.5 | 2.9 |
| Succinic acid diamide | 1.1 | 2.1 |
| Adipic acid diamide | 7.0 | 14 |
| Acrylamide | 4.0 | 7.7 |
| Benzylamide | 2.6 | 5.2 |
| Nicotinamide | 8.5 | 19 |

2. Amino Acid Amides and α-hydroxycarboxylic Acid Amides

For prolinamide, and the α-hydroxycarboxylic acid amides lactic acid amide (Lac-$NH_2$) and 2-hydroxy-4-methylmercaptobutyric acid amid (MHA-$NH_2$), the methionine-analogous α-hydroxycarboxylic acid amide, determination of the product with the previous HPLC analysis is not possible. For these substrates, the activity was determined with the aid of $NH_4^+$ determination. The enzyme used was a partly purified D-amidase after the 2nd chromatography step with a specific activity of 0.56 U/mg. All the substrates were employed in the enzyme test at 40 mM. In the 4th column, for further comparison the activity for the lower enantiomer has been set at 1 and a relative activity for the preferred enantiomer has been calculated therefrom.

TABLE 2

Enzyme activities for amino and hydroxy acid amides

| Substrate | Relative act. [U/mg] | Activity with respect to Tle-$NH_2$ | Rel. activity with respect to D and L |
|---|---|---|---|
| DL-Tle-$NH_2$ | 0.56 | 1 | — |
| D-Ala-$NH_2$ | 23 | 44 | 3.0 |
| L-Ala-$NH_2$ | 7.7 | 15 | 1 |
| D-Leu-$NH_2$ | 220 | 400 | 15 |
| L-Leu-$NH_2$ | 15 | 26 | 1 |
| D-Val-$NH_2$ | 6.9 | 13 | 11 |
| L-Val-$NH_2$ | 0.59 | 1.2 | 1 |
| L-Ile-$NH_2$ | 0.17 | 0.35 | — |
| D-Phe-$NH_2$ | 500 | 890 | 4.6 |
| L-Phe-$NH_2$ | 110 | 190 | 1 |
| L-Tyr-$NH_2$ | 47 | 100 | — |
| DL-Trp-$NH_2$ | 86 | 160 | 2.5 |
| L-Trp-$NH_2$ | 34 | 62 | 1 |
| DL-Met-$NH_2$ | 130 | 230 | 2.7 |
| L-Met-$NH_2$ | 48 | 86 | 1 |
| D-Pro-$NH_2$ | 12 | 24 | 1 |
| L-Pro-$NH_2$ | 28 | 56 | 2.3 |
| D-Lac-$NH_2$ | 29 | 59 | 1 |
| L-Lac-$NH_2$ | 33 | 66 | 1.1 |
| DL-MHA-$NH_2$ | 82 | 150 | — |

The suitability of the D-amidase for kinetic cleavage of racemic DL-Tle-$NH_2$ in accordance with the following equation was also investigated.

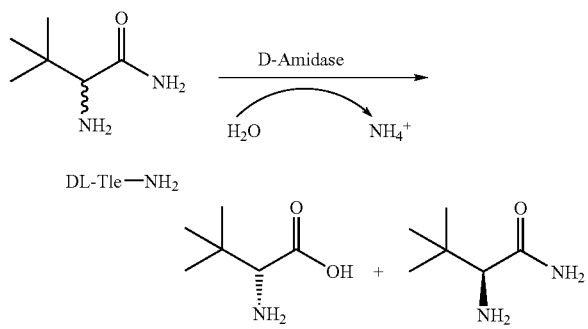

To evaluate the suitability for kinetic cleavage of racemic DL-Tle-NH$_2$, the enantioselectivity was determined as a function of the conversion. With partly purified enzyme after the 1st chromatography step (ion exchange chromatography: Q-Sepharose FF (Pharmacia)), at a conversion of greater than 45% enantioselectivities of 96.6% with respect to D-Tle were already determined. With virtually homogeneous enzyme, ee values of between 99.4 and 98.6% were measured in the range from 45 to 50% conversion. For both series of experiments, an E value (Straathof, A. J. J. and Jongejan, J. A. (1997), The enantiomeric ratio: origin, determination and prediction, Enzyme Microb. Technol. 21, 559–571) of greater than 100 is thus calculated. This is a very good basis for cleavage of racemates with a virtually complete conversion of the D-enantiomer.

DL-Valin-, DL-leucin- and DL-phenylalaninamide were also tested in this respect. For this, the enantioselectivity was determined as function of the conversion with partly purified enzyme from *Variovorax paradoxus* 19-3 after the 1st chromatography step. FIG. 1 shows the enantioselectivity for D-Val, D-Leu and D-Phe as a function of the conversion.

Some measurement values, in particular in the region of 50% conversion and the E values calculated therefrom, are listed by way of example in the following table.

TABLE 3

Enantioselectivities for D-Val, D-Leu and D-Phe

| Conversion [%] | ee D-Val [%] | E value |
|---|---|---|
| DL-Val-NH$_2$ | | |
| 3 | 98.9 | 190 |
| 15 | 98.7 | 180 |
| 29 | 98.5 | 200 |
| 42 | 98.1 | 220 |
| 50 | 95.1 | 140 |
| 57 | 75.0 | 56 |
| DL-Leu-NH$_2$ | | |
| 4 | 99.6 | 470 |
| 18 | 98.1 | 130 |
| 33 | 97.3 | 120 |
| 40 | 96.7 | 114 |
| 48 | 90.8 | 53 |
| 51 | 86.7 | 41 |
| DL-Phe-NH$_2$ | | |
| 4 | 68.8 | 5.6 |
| 14 | 65.1 | 5.2 |
| 26 | 61.5 | 5.1 |
| 36 | 58.3 | 5.2 |
| 51 | 50.9 | 5.1 |

In the range from 40 to 50% conversion, enantioselectivities for D-Val in the range from 98.1 to 95.1%, for D-Leu in the range from 96.7 to 90.8% and for D-Phe in the region of 55% result. For racemic Val-NH$_2$ and Leu-NH$_2$ average E values greater than 100 are calculated, and for Phe-NH$_2$ an E value of 5.

With respect to the cleavage of racemates with a desired virtually complete conversion of the D-enantiomer, the D-amidase is thus very particularly suitable in principle for DL=Val-NH$_2$ and DL-Leu-NH$_2$.

Extension of the substrate spectrum:

The cleavage of racemic N-formylated amino acid amides was investigated by using the D-amidase according to the invention. The enzyme used was a partly purified D-amidase after the 1st chromatography step. The activity was measured by determining the NH$_4^+$ ions with glutamate dehydrogenase (Bergmeyer, H. U., and Beutler, H.-O. (1985), Ammonia. In: Methods of Enzymatic Analysis. VCH-Verlag, 3rd edition, vol. 8: 454–461, Weinheim). The following substrates were employed in the enzyme test at 10 mM.

TABLE 4

Relative enzyme activities for N-formylated Val-NH$_2$

| Substrate | Relative act. [mU/mg] | Activity with respect to Tle-NH$_2$ [%] |
|---|---|---|
| DL-Tle-NH$_2$ | 200 | 100 |
| DL-Formyl-Val-NH$_2$ | 670 | 280 |

The conversion of racemic N-formyl-valinamide was better than DL-Tle-NH$_2$ by a factor of 2.8.

TABLE 5

Comparison of the enzyme activities of valinamide and N-formyl-valinamide

| Substrate | Relative act. [mU/mg] | Activity with respect to Tle-NH$_2$ [%] |
|---|---|---|
| DL-Val-NH$_2$ | 870 | 100 |
| DL-Formyl-Val-NH$_2$ | 670 | 77 |

Figure 2:
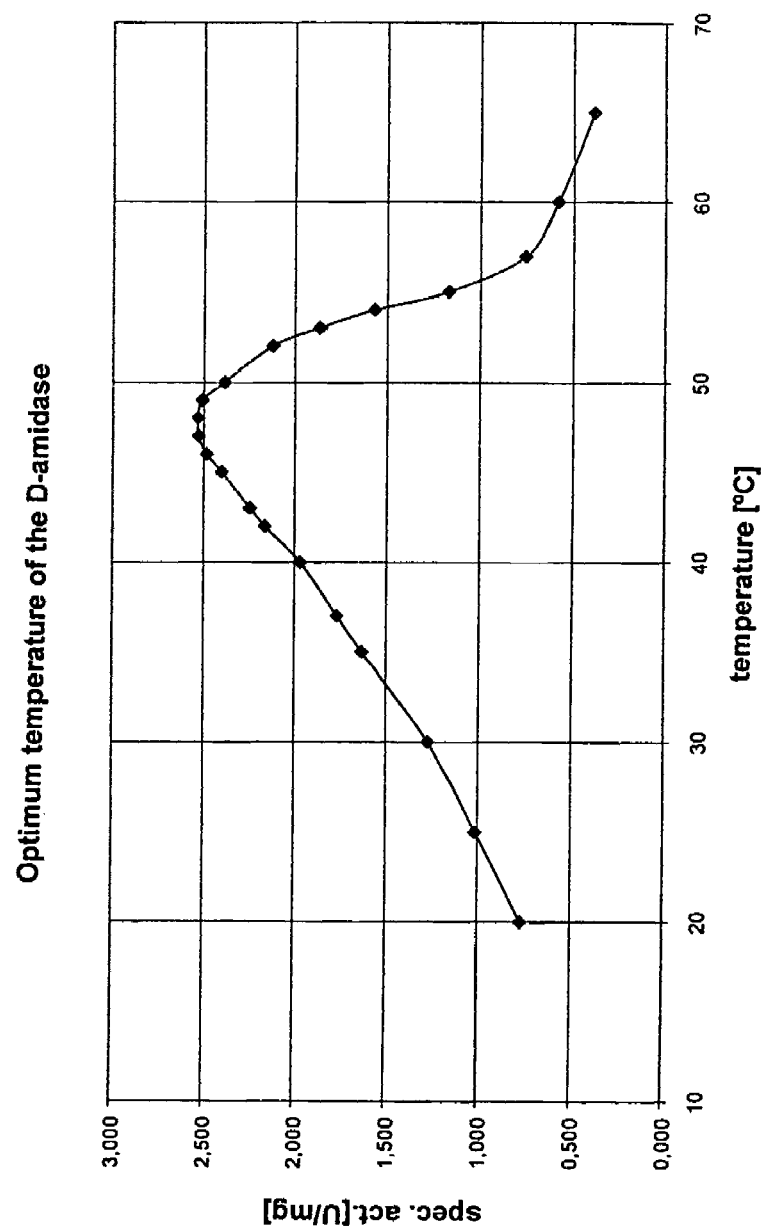
FIG. 2 shows the effect of temperature on enzyme activity.
Figure 3:
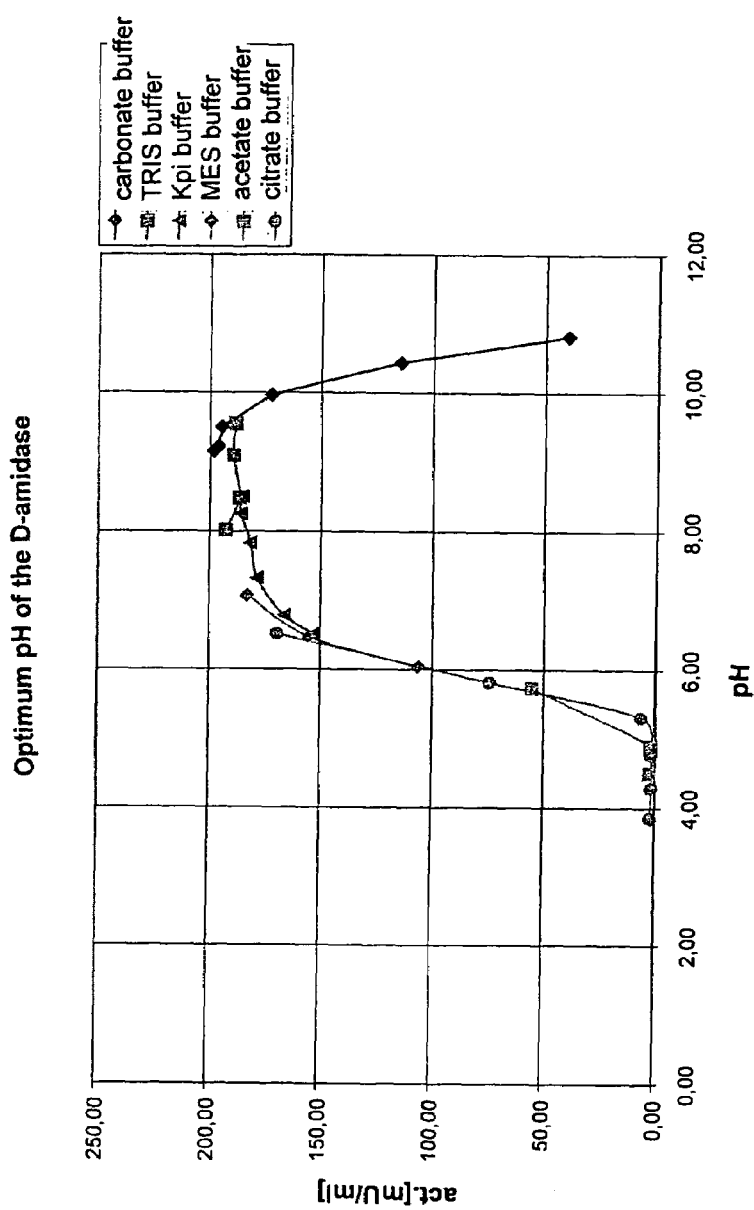
FIG. 3 shows the effect of pH on enzyme activity.

Optimum temperature and pH of the D-amidase:

FIGS. 2 and 3 show the dependence of the activity on the temperature and pH. An optimum temperature in the region of 47 and 48° C. results from this for the D-amidase. FIG. 3 shows a broad optimum pH in the range from 7.5 to 9.5 with about the same activity. The highest activity was determined in sodium carbonate buffer at pH 9.

A comparison of the entire amino acid sequence of the D-amidase according to the invention with existing amidases in protein databanks at NCBI via the Internet (http://www.ncbi.nlm.nih.gov/blast with the program BLASTP 2.2.1, database: nr, pat, SwissProt) leads to similarities with a large number of known amidases. In the best case, the similarity of the amino acid sequence is found to be 66% (303/457 AA) and 50% identical (229/457 AA) to a possible amidase from *Mycobacterium tuberculosis*, (gi: 6225047; Cole, S. T. et al. (1998), Deciphering the biology of *Mycobacterium tuberculosis* from the complete genome sequence, Nature 393, 537–544). The enantioselective amidase from *Rhodococcus* sp. at 52% and 37% is the second most similar protein (gi: 152052; Mayaux, J.-F.; Cerbelaud, E.; Soubrier, F.; Yeh, P.; Blanche, F.; Pétré, D. (1991), Purification, Cloning, and Primary Structure of a New Enantiomer-Selective Amidase from a *Rhodococcus* Strain: Structural Evidence for a Conserved Genetic Coupling with Nitrile Hydratase, J. Bacteriol. 173, 6694–6704) which also already has a high homology on comparison of the N-terminus with the D-amidase.

In the case of the present invention, this is thus a new D-amidase with the ability inter alia to convert DL-Tle-$NH_2$ into D-Tle in excellent ee values and yields. Since these optical antipodes of the amino acid were hitherto accessible only with difficulty, description of the new D-amidases denotes an important step towards the industrial preparation of this non-natural amino acid, which can preferably be used in bioactive peptide mimetics.

EXAMPLES

1. Culture of the Strain *Variovorax paradoxus* DSM 14468 for Induction of the D-amidase For induction of the D-amidase, the strain *Variovorax paradoxus* 19-3 DSM 14468 was cultured in a minimal medium with racemic Tle-$NH_2$ as the source of nitrogen; composition of the minimal medium:

TABLE 6

Minimal medium for Variovorax paradoxus
Minimal medium

| | |
|---|---|
| $KH_2PO_4$ | 3.30 g |
| $K_2HPO_4$ | 0.80 g |
| NaCl | 1.00 g |
| $CaCl_2$ | 0.05 g |
| $MgSO_4 \times 7\ H_2O$ | 0.30 g |
| D,L-tert-Leucinamide | 3.30 g |
| Glucose | 4.50 g |
| Trace salt solution | 0.80 ml |
| Vitamin solution | 2.50 ml |
| Aq. demin. | to 1,000 ml; pH 7.3 |

TABLE 7

Composition of the trace salt solution
Trace salt solution

| | |
|---|---|
| $H_3BO_3$ | 75.0 mg |
| $MnCl_2 \times 4\ H_2O$ | 50.0 mg |
| $ZnCl_2$ | 187.5 mg |
| $CuSO_4 \times 5\ H_2O$ | 50.0 mg |
| $FeCl_3$ | 625.0 mg |
| $(NH_4)_6Mo_7O_{24} \times 4\ H_2O$ | 25.0 mg |
| $CoCl_2 \times 6\ H_2O$ | 37.5 mg |
| $NiCl_2 \times 6\ H_2O$ | 50.0 mg |
| Aq. demin. | to 200 ml |

TABLE 8

Composition of the vitamin solution
Vitamin solution

| | |
|---|---|
| Biotin | 0.20 mg |
| Nicotinic acid | 2.00 mg |
| Thiamine | 1.00 mg |
| 4-Aminobenzoate | 1.00 mg |
| Pantothenate | 0.50 mg |
| Pyridoxamine | 5.00 mg |
| Cyanocobalamin | 2.00 mg |
| Aq. demin. | to 100 ml |

The sterilization was carried out by autoclaving at 121° C. under 1.2 bar for 20 minutes. Since glucose, $CaCl_2$, $MgSO_4 \times 7H_2O$, vitamin solution and DL-Tle-$NH_2$ react sensitively to this type of sterilization, they were added to the nutrient solutions only after the autoclaving but were first filter sterilized with 0.2 μm membranes (Sartorius).

2. Obtaining Crude Extracts From *Variovorax paradoxus* and *E. coli*

After harvesting by centrifugation, the cultures were washed once with potassium phosphate buffer, 100 mM pH 7.5 and adjusted to a 20% cell suspension. The cell breakdown on an analytical scale was carried out either by wet grinding using a vibratory mill from Retsch (Hummel, W.; Kula, M.-R. (1989), A Simple Method for Small-Scale Disruption of Bacteria and Yeasts, J. Microbiol. Methods 9, 201–209) or by ultrasound by means of a Pulses Sonifier from Branson.

To lower protease activities, all further working steps were carried out at 4° C. The Bradford protein content determination (Bradford, M. M. (1976), A Rapid and Sensitive Method for the Quantitation of Microgram Quantities of Protein Utilizing the Principle of Protein-Dye Binding, Anal. Biochem. 72, 248–254) in the crude extract enabled the quality of the breakdown to be evaluated.

Wet Grinding Using a Vibratory Mill:

1.2 g of glass beads (diameter 0.3 mm) and 0.6 ml of cell suspension were introduced into 1.5 ml Eppendorf cups and were broken down with a vibratory mill for ten minutes at maximum vibration frequency. The glass beads and cell debris were separated from the cell homogenate by centrifugation for ten minutes at 10,000 rpm and 4° C. and the supernatant was employed as the crude extract in the enzyme test.

Ultrasonic Breakdown:

*Variovorax paradoxus* cultures were broken down in portions of a maximum of 10 ml with 8×60 s bursts at 70% pulse, 80% intensity and in each case 60 seconds of intermediate cooling. *E. coli* cultures were broken down in 1 ml portions with 4×60 sseconds bursts at 70% pulse, 80% intensity and in each case 60 seconds of intermediate cooling. The cell homogenate was centrifuged off and the crude extract was taken off.

The breakdown for purification of the D-amidase from *Variovorax paradoxus* in volumes of between 20 and 200 ml was carried out in a Disintegrator S from IMA. For this, the cell suspension and glass beads (diameter 0.3 mm) were mixed in a ratio of 1:1.5 and the cells were broken down for 20 min at 3,500 rpm.

2. Culturing *Variovorax paradoxus* DSM 14468. DSMZ Complete Medium No. 1 and Preparation of the Genomic DNA For this, the strain *Variovorax paradoxus* was cultured in DSMZ Complete Medium No. 1 to an optical density $OD_{660}$ of approx. 1.0; composition (DSMZ, Catalogue of Strains (1998), Braunschweig):

TABLE 9

Composition of DSMZ Complete Medium No. 1
DSMZ Complete Medium No. 1

| | |
|---|---|
| Peptone | 5.0 g |
| Meat extract | 3.0 g |
| Aq. demin. | to 1,000 ml; pH 7.0 |

The culture was harvested under sterile conditions and washed once with sterile potassium phosphate buffer 20 mM pH 6.5. The genomic DNA was prepared by with the DNeasy™ Tissue Kit (Qiagen). The preparation was carried out in accordance with the protocol for Gram-negative bacteria from the Qiagen DNeasy™ Tissue Kit Handbook (4/99).

3. Oligonucleotides

TABLE 10

List of the oligonucleotides used

| Description: | Use: | Sequence: | SEQ ID |
|---|---|---|---|
| AAH-N1 | PCR | 5' GTS GGC CGS CGS ATC CAG CAG AAG GA 3' | 3 |
| AAH-C1 | PCR | 5' GGG ATS CGG ATC GAG CCG CCS GTS TC 3' | 4 |
| AAH-GW-F1 | PCR | 5' GCG TCA CGC CGC CGG TCA ATC CGT GGA A 3 | 6 |
| AAH-GW-R1 | PCR | 5' CAG CGC GTG TTC GGC CAT CAC GAT CAC ATA 3' | 7 |
| AAH-GW-F2 | PCR | 5' GGC GCA CTG GTC GGG TGC CTC GTC GA 3' | 8 |
| AAH-GW-R2 | PCR | 5' CTC TTG AGC GCG CCG TCG ACC TTC TCG A 3' | 9 |
| AAH-K-N2 | PCR | 5' CTG GTC ATC AAG CGC GGC CAG ATC GGC 3' | 10 |
| AAH-K-C2 | PCR | 5' GAT CGG CCG ACA GCC GAT TGG CCA GC 3' | 11 |
| AAH-N-EcoRI | PCR | 5' CCG GAA TTC ATG AGC AAC GAA CTG CAT TAC CT 3' | 12 |
| AAH-C-hindIII | PCR | 5' ATC CCA AGC TTT TAG AGC ACC GGA TGC CG 3' | 13 |

The designation S represents G+C in the sequence of AAH-N1 and AAH-C1 (IUB group code for identification of redundancies).

4. Genetic Engineering Methods

All the genetic engineering methods used here, unless noted otherwise, are described by Sambrook et al. (1989), Molecular cloning: a laboratory manual, 2nd ed., Cold Spring Harbor Laboratory Press, New York and Hopwood et al. (1985), Genetic manipulation of Streptomycetes: A laboratory manual, The John Innes Foundation, Norwich). All the enzymes and corresponding buffers were used in accordance with the manufacturer's instructions. Sequencing was carried out by Sequiserve, Vaterstetten.

5. Polymerase Chain Reaction (PCR)

DNA amplifications by the polymerase chain reaction were carried out with the Biometra Personal Cycler™ (Göttingen) in accordance with the method of Saiki et al. (1988), Primer-directed enzymatic amplification of DNA with a thermostable DNA polymerase, Science 239; 487–491. The heat-stable DNA polymerases Vent$_R$® (New England Biolabs) and Herculase™ (Stratagene) and the buffers supplied by the manufacturer were used. The primer pairs used are listed in table 10.

By the PCR, initially a fragment of the D-amidase gene 509 bp in size, and after the entire gene sequence of the D-amidase was present the entire D-amidase gene was amplified from genomic DNA by the GenomeWalker method (Stratagene). After securing and checking of this D-amidase gene sequence in the vector pUC18, plasmid DNA was used as the template.

TABLE 11

Composition of a PCR batch for genomic or plasmid DNA PCR batch:

| | |
|---|---|
| Genomic DNA or | 100–500 ng |
| plasmid DNA | 20 ng |
| Polymerase buffer (10x) | 1/10 vol. |
| dNTPs | each 0.2 mM |
| Sense and antisense primer | each 10–50 pmol |
| DNA polymerase | 1–5 U |
| DMSO | 5% (v/v) |
| Aq. demin. | to 50 µl |

The PCR batches were covered with a layer of approx. 50 µl of light mineral oil. For the PCR programmes, the annealing temperature TA was determined via the DNA melting temperature (Tm) of the oligonucleotides. The time X for the chain reaction of the DNA polymerase followed the 1 kb=1 min rule.

TABLE 12

PCR programme for a 0.5 kb fragment of the D-amidase gene (SEQ ID NO:5) with the primer pair AAH-N1/AAH-C1

| Step | Temperature | Time |
|---|---|---|
| 1 | 95° C. | 5 min |
| 2 | 95° C. | 1 min |
| 3 | 70–61° C. | 45 sec |
| 4 | 72° C. | 30 sec |
| 5 | 95° C. | 1 min |
| 6 | 70° C. | 45 sec |
| 7 | 72° C. | 30 sec |
| 8 | 72° C. | 2 min |

Steps 2–4 were passed through 10 times, the annealing temperature of step 3 being lowered by −1° C. per cycle. Steps 5–7 were then passed through 20 times.

TABLE 13

PCR program for the entire D-amidase gene (SEQ ID NO:1) with 92 bp before the start codon and 80 bp after the stop codon with the primer pair AAH-K-N2/AAH-K-C2

| Step | Temperature | Time |
|---|---|---|
| 1 | 95° C. | 5 min |
| 2 | 95° C. | 45 sec |
| 3 | 70° C. | 2.5 min |
| 4 | 95° C. | 45 sec |
| 5 | 67° C. | 2.5 min |
| 6 | 67° C. | 5 min |

Steps 2–3 were passed through 10 times and then steps 4–5 were passed rough 20 times.

TABLE 14

PCR programme for the introduction of an EcoRI cleavage site at the 5' end and a HindIII cleavage site at the 3' end of the D-amidase gene with the primer pair AAH-N-EcoRI/AAH-C-HindIII:

| Step | Temperature | Time |
|---|---|---|
| 1 | 95° C. | 5 min |
| 2 | 95° C. | 1 min |
| 3 | 52–41° C. | 1 min |
| 4 | 70° C. | 2 min |
| 5 | 95° C. | 1 min |
| 6 | 62° C. | 1 min |
| 7 | 70° C. | 2 min |
| 8 | 70° C. | 5 min |

Steps 2–4 were passed through 12 times, the annealing temperature of step 3 being lowered by −1° C. per cycle. Steps 5–7 were then passed through 20 times.

The purification and isolation of the PCR products were carried out either directly by means of the PCR Purification Kit (Qiagen) or by agarose gel electrophoresis of the entire PCR batch and subsequent isolation of the DNA fragment by means of the QIAquick Gel Extraktion Kit (Qiagen).

6. Universal GenomeWalker™ Method (Clontech) for Discovery of the Entire D-amidase Gene With the aid of the fragment of the D-amidase gene 509 bp in size (SEQ ID NO;5), the Universal GenomeWalker™ Kit enabled PCR-mediated cloning of the entire D-amidase gene starting from genomic DNA from *Variovorax paradoxus*. Using a "GenomeWalker library", genomic DNA was hydrolysed with four different restriction enzymes (EcoR V, Sca I, Pvu II and Stu I). After purification of the DNA restriction batches, in each case a blunt-end ligation followed with the GenomeWalker adapters included, for which two adapter primers (AP1 and AP2) existed. The genomic DNA restriction and the ligation of the adapters were carried out in accordance with the Universal GenomeWalker™ Kit User Manual (3/2000, Clontech). This library served as a template for a first PCR reaction (primary PCR). For in each case a PCR reaction in both directions, the primer pairs AP1/AAH-GW-F1 (downstream) and AP1/AAH-GW-R1 (upstream) were used. Herculase® (Stratagene) was employed as the DNA polymerase to enable amplification of large DNA fragments ("long-distance PCR").

TABLE 15

Composition of the 1st PCR, GenomeWalker™ method PCR batch:

| | |
|---|---|
| GenomeWalker library | 2 µl |
| Polymerase buffer (10x) | 1/10 vol. |
| dNTPs | each 0.2 mM |
| Sense and antisense primer | 50 pmol |
| DNA polymerase | 2.5 U |
| DMSO | 5% (v/v) |
| Aq. demin. | to 50 µl |

The PCR batches were covered with a layer of approx. 50 µl of light mineral oil.

TABLE 16

PCR program for the 1st PCR, GenomeWalker™ method with the primer pair AP1/AAH-GW-F1 or AP1/AAH-GW-R1

| Step | Temperature | Time |
|---|---|---|
| 1 | 95° C. | 2 min |
| 2 | 95° C. | 30 sec |
| 3 | 70° C. | 4 min |
| 4 | 95° C. | 30 sec |
| 5 | 67° C. | 4 min |
| 6 | 67° C. | 10 min |

Steps 2–3 were passed through 10 times. Steps 4–5 were then passed through 25 times, the duration of step 5 being lengthened by 10 sec per cycle (time increment). A second PCR (secondary or nested PCR) was carried out with the PCR products obtained, using the primer pairs AP2/AAIH-GW-F2 (downstream) and AP2/AAH-GW-R2 (upstream), by which formation of non-specific PCR products can be minimized. The PCR amplification products were diluted down to 1:50, depending on the concentration, with aq. demin. and employed in this form as templates.

TABLE 17

Composition of the 2nd PCR, GenomeWalker™ method PCR batch:

| | |
|---|---|
| PCR product of the 1st PCR | 1 ml |
| Polymerase buffer (10x) | 1/10 vol. |
| dNTPs | each 0.2 mM |
| Sense and antisense primer | 50 pmol |
| DNA polymerase | 2.5 U |
| DMSO | 5% (v/v) |
| Aq. demin. | to 50 µl |

The PCR batches were covered with a layer of approx. 50 µl of light mineral oil.

TABLE 18

PCR program for the 2nd PCR, GenomeWalker™ method with the primer pair AP2/AAH-GW-F2 or AP2/AAH-GW-R2

| Step | Temperature | Time |
|---|---|---|
| 1 | 95° C. | 2 min |
| 2 | 95° C. | 30 sec |
| 3 | 70° C. | 4 min |
| 4 | 95° C. | 30 sec |
| 5 | 67° C. | 4 min |
| 6 | 67° C. | 10 min |

Steps 2–3 were passed through 10 times and then steps 4–5 were passed through 20 times.

The resulting PCR products of the 2nd PCR were separated in an agarose gel and the predominant amplification product was purified and sequenced as described. Summarizing, starting from the GenomeWalker library, the following PCR amplification products thus resulted after the 2nd PCR:

TABLE 19

PCR products after the 2nd PCR, GenomeWalker™ method

| GenomeWalker library | Size of the 2nd PCR product |
|---|---|
| Downstream direction | |
| EcoR V library | 1.6 kb |
| Pvu II library | 3.5 kb |
| Sca I library | 1.2 kb |
| Stu I library | 1.4 kb |
| Upstream direction | |
| EcoR V library | no amplification product |
| Pvu II library | 0.5 kb |
| Sca I library | no amplification product |
| Stu I library | 1.8 kb |

Figure 4:
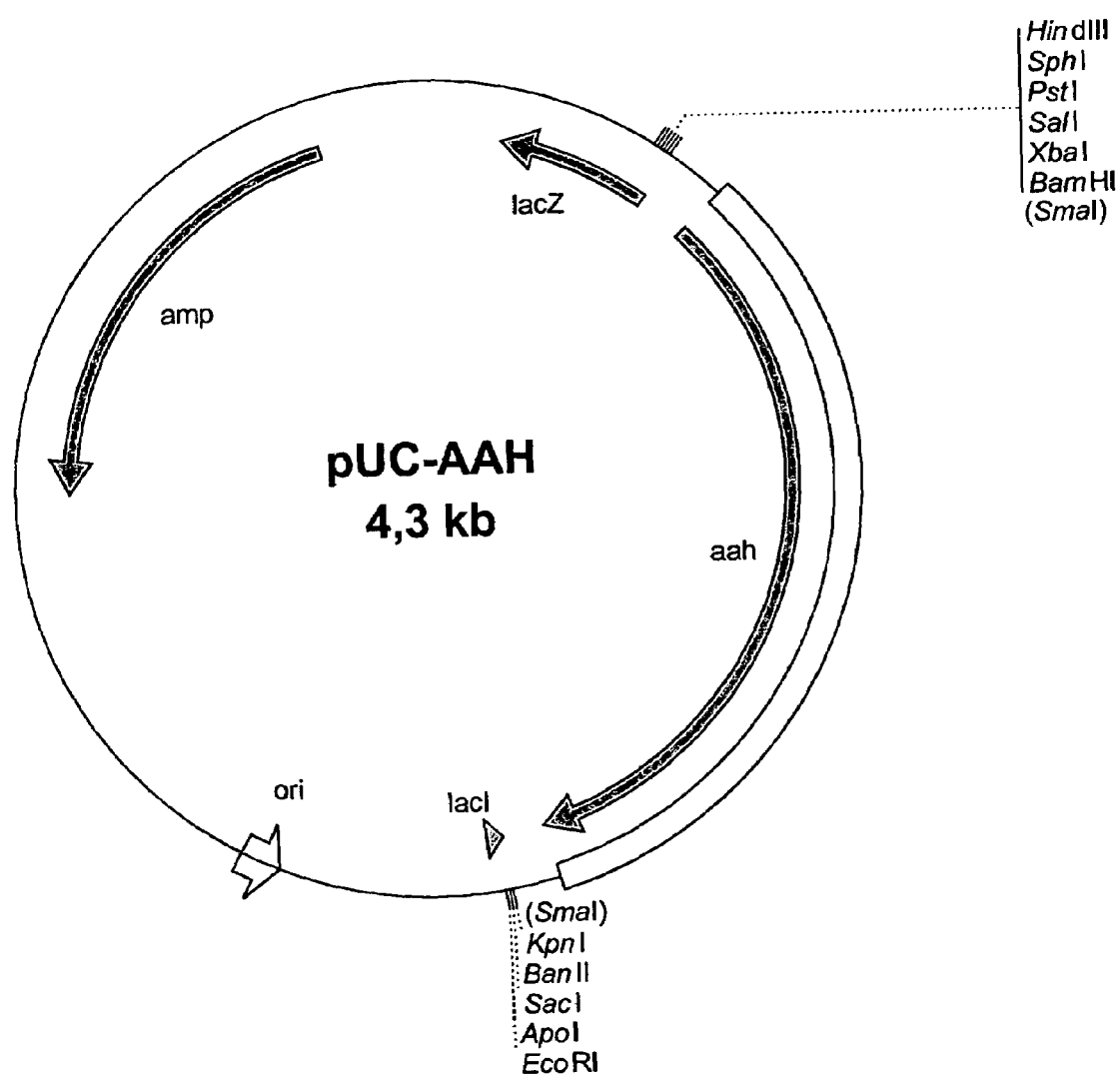
FIG. 4 shows a plasmid map of pUC-AAH.

6. Ligation of the PCR Products Into the Vector pUC18 and Subsequent Cloning in E. coli XL1 Blue For further working, the PCR products from three parallel batches with the entire D-amidase gene with 92 bp before the start codon and 80 bp after the stop codon were ligated into the vector pUC18 (Roche Biochemicals) and transformed in E. coli XL1 Blue. These techniques are described in detail in Sambrook et al.(1989), Molecular cloning: a laboratory manual, 2nd ed., Cold Spring Harbor Laboratory Press, New York and Hopwood et al. (1985), Genetic manipulation of Streptomycetes: A laboratory manual, The John Innes Foundation, Norwich. The D-amidase gene sequence (SEQ ID NO:1) of the plasmids was checked by sequencing and was identical for the three batches. The plasmid was called pUC-AAH (FIG. 4). A plasmid map of pUC-AAH is shown in FIG. 4. The PCR product 1.6 kb in size with the aah gene and 92 bp before the start codon and 80 bp after the stop codon in pUC18 is shown. (Primer pair: AAH-K-N2/AAH-K-C2)

7. Heterologous Expression of the D-amidase Enzyme From Variovorax paradoxus in E. coli JM 101

As already described under 5., starting from the plasmid pUC-AAH for an expression of the D-amidase by means of the PCR reaction, an EcoRI cleavage site was introduced at the 5' end and a HindIII cleavage site at the 3' end and the PCR product was ligated into the pBTAC vector and transformed in the expression strain E. coli JM 101.

The standardized heterologous expression was carried out in accordance with the method of Sambrook et al. (1989), Molecular cloning: a laboratory manual, 2nd ed., Cold Spring Harbor Laboratory Press, New York.

The transformed E. coli JM 101 derivatives were incubated in LB medium (with 0.1 mg/ml) overnight at 37° C. 30 ml cultures (LB medium with 0.1 mg/ml ampicillin in 4 baffle flasks) were then inoculated with 0.3 ml of overnight culture (1:100). Expression of the amidase was induced at a cell density of $OD_{600nm}$=0.4–0.6 with 30 µl of a 1 M IPTG solution (concentration in the culture 1 mM; IPTG=isopropyl thioglactoside). After incubation for a further 4–6 h at 30° C., the cells were harvested. In crude extracts of the expression clones cultured in the manner described above, a D-amidase activity of 80–210 mU/mg of total protein was to be determined for DL-Tle-NH$_2$ as the substrate.

8. Demonstration of the D-amidase Activity

In the conversion of tert-leucinamide (gen. acid amides) by the D-amidase, the formation of ammonia or ammonium ions and tert-leucine (gen. acid) in equimolar amounts occurs. The determination of the increase in ammonium ions and the tert-leucine formation by means of HPLC was thus used to demonstrate the amidase activity. The change in concentration of the components participating can be measured in an enzyme test, which comprises incubation of the following test batch for 10–60 minutes at 30° C.

TABLE 20

Composition of the enzyme test

| Enzyme test | Volume [µl] |
|---|---|
| Potassium phosphate buffer (0.1 M, pH 7.5) | 400 |
| D,L-tert-Leucinamide (0.2 M) | 50 |
| Crude extract or purified enzyme solution | 50 |
| Total volume | 500 |

The enzyme test was started by addition of the substrate and the reaction was stopped by heating at 95° C. for three minutes. The analysis of the reaction products was carried out for ammonium ions by enzymatic determination of ammonium by glutamate dehydrogenase (Bergmeyer, H., U., and Beutler, H.-O. (1985) Ammonia. In: Methods of Enzymatic Analysis. VCH-Verlag, 3rd edition, vol. 8: 454–461, Weinheim) and for D- and L-tert-leucine by means of HPLC (Brückner, H., Wittner R., and Godel H., (1991) Fully automated high-performance liquid chromatographic separation of DL-amino acids derivatized with o-phthaldialdehyde together with N-isopropyl-cysteine. Application to food samples. Anal. Biochem. 144(1): 204–206). Batches to which no substrate were added served as controls.

9. Enzymatic Determination of the Ammonium Ions by Means of Glutamate Dehydrogenase The enzyme glutamate dehydrogenase (GluDH; E.C. 1.4.1.3) converts 2-oxoglutarate into L-glutamate, ammonium ions being consumed and NADH being oxidized to NAD+(Bergmeyer, H., U. and Beutler, H.-O. (1985), Ammonia. In: Methods of Enzymatic Analysis. VCH-Verlag, 3rd edition, vol. 8: 454–461, Weinheim). The amount of NADH consumed during the reaction is equivalent to the amount of ammonium ions. The change in the concentration of NADH is the measurement parameter and can be determined spectrophotometrically at a wavelength of 340 nm.

Test solutions: 2-Oxoglutarate/ADP/TEA buffer: 9.3 g TEA, 95 mg ADP, 670 mg 2-oxoglutarate in aq. demin. to 100 ml, pH 8.0

NADH solution: 30 mg NADH, 60 mg NaHCO$_3$ dissolved in 6 ml aq. demin.

Glutamate dehydrogenase: from bovine liver in 50% glycerol, 120 U/mg

TABLE 21

Composition of the ammonium ion determination by
means of glutamate dehydrogenase

| Test procedure | Volume [µl] |
|---|---|
| 2-Oxoglutarate/ADP/TEA buffer | 500 |
| NADH solution | 50 |
| Sample solution | 100 |
| Aq. demin. | 950 |
| Total volume | 1,600 |

The test components were pipetted into cells of plastic (1.5 ml semimicro disposable cells, Brand) and mixed and the extinction at 340 nm was determined after 5 min. 10 µl GluDH were then added, and after the reaction had gone to completion, as a rule after 30 min, the extinction was measured again.

The change in extinction ΔE was obtained by subtraction of the second value from the first. A measurement range up to 2 mM ammonium ions results for the particular samples.

A comparison between sample batches and associated controls gave information on whether the values measured were to be attributed to ammonium ions liberated from D,L-Tle-NH$_2$ or those already present in the crude extract.

By plotting a calibration line by means of defined amounts of ammonium chloride, it was possible to determine the ammonium ion concentration from the changes in extinction.

10. OPA/IBC Derivatization for the Determination of D- and L-tert-leucine by Means of HPLC The separation and quantitative determination of the enantiomers D- and L-tert-leucine were carried out by a "chiral derivatization" on the basis of o-phthaldialdehyde (OPA)/N-isobutyryl-L-cysteine or N-isobutyryl-D-cysteine (Brückner, H.; Wittner R. and Godel H. (1991), Fully automated high-performance liquid chromatographic separation of DL-amino acids derivatized with o-Phthaldialdehyde together with N-isopropyl-cysteine. Application to food samples. Anal. Biochem. 144, 204–206). The diastereomeric isoindole derivatives formed were separated on an RP-18 (reversed phase) column and detected by fluorescence. A two-buffer system of aqueous acetate buffer and an acetonitrile/water mixture was used as the mobile phase.

Chromatography Conditions:
Stationary phase: Kromasil™ HPLC column, 250×4 mm, 5 □m, 100 Å (Eka Nobel)
Mobile phase:
Mobile phase A: 23 mM sodium acetate, pH 6.0
Mobile phase B: acetonitrile (HPLC grade) and aq. demin.: 10:1.5 (v,v)
Flow rate: 1 ml/min
Sample volume: 20 µl
Detection: Fluorescence: ex. 340 nm/em. 440 nm

TABLE 22

Gradient programme of the HPLC
Gradient program:

| Time [min] | Mobile phase B [%] |
|---|---|
| 0 | 23 |
| 25 | 28 |
| 27 | 100 |
| 30 | 100 |
| 32 | 0 |
| 42 | 0 |

11. Purification of the D-Amidase From *Variovorax paradoxus*

The purification of the D-amidase was carried out in three chromatography steps after cell breakdown.

Ion exchange chromatography:
Column material: Q-Sepharose FF (Pharmacia)
Buffer A: potassium phosphate buffer, 20 mM, pH 6.5
Buffer B: buffer A+150 mM Na$_2$SO$_4$
Elution over a linear gradient 2. Hydrophobic Interaction Chromatography:
Column material: Butyl-Sepharose 4 FF (Pharmacia)
Buffer A: potassium phosphate buffer, 20 mM, pH 6.5+150 mM Na$_2$SO$_4$
Buffer B: potassium phosphate buffer, 20 mM, pH 6.5
Elution over a linear gradient 3. Gel Filtration Chromatography:
Column material: Superdex 200 PG (Pharmacia)
Buffer: potassium phosphate buffer, 20 mM, pH 6.5+180 mM NaCl After the 2nd step usually only a very low content of foreign protein is still present. A yield of 88% can be calculated for the first two purification steps, a spec. act. of 0.68 U/mg for DL-Tle-NH$_2$ being present. For the homogeneously purified D-amidase from *Variovorax paradoxus*, a spec. act. of 1.4 U/mg for DL-Tle-NH$_2$ resulted.

12. Determining the Optimum Temperature of the D-amidase

Virtually homogeneously purified enzyme with a specific activity of about 1.3 U/mg was used for determination of the optimum temperature. A determination of the activity, as described under 8., with DL-Tle-NH$_2$ as the substrate was carried out from 20° to 50° C. in 5° C. steps, the range from 40° to 55° C. being investigated in more detail with further measurements. The incubation time chosen was relatively short at 15 min. The course of the activity as a function of the temperature is shown in FIG. 2.

13. Determination of the Optimum pH of the D-amidase

For this, the activity was determined with the partly purified enzyme, after the ion exchange chromatography, at pH values in the range from 3.5 to 11 using the following buffer substances.

TABLE 23

Buffers for determination of the optimum pH

| pH range | Buffer substance [100 mM] |
|---|---|
| 3.5–6.0 | Na citrate |
| 4.0–5.0 | Na acetate |
| 5.0–6.5 | MES |
| 5.5–8.5 | Kpi |

TABLE 23-continued

Buffers for determination of the optimum pH

| pH range | Buffer substance [100 mM] |
|---|---|
| 8.0–9.5 | TRIS |
| 8.5–11.0 | Na carbonate |

The determination of the activity was carried out, as described under 8., with DL-Tle-NH$_2$ as the substrate and an incubation of 30 min at 30° C. The course of the activity as a function of the pH and the particular buffer substance is shown in FIG. 3.

The present application claims priority to DE 101 60 066.6 filed on Dec. 6, 2001, the contents of which are incorporated herein by reference.

The invention claimed is:

1. An isolated polypeptide, which comprises SEQ ID NO:2.

2. A method of making a carboxylic acid, comprising contacting a carboxylic acid amide with the isolated polypeptide of claim 1.

3. The method of claim 2, wherein the carboxylic acid is an amino acid and the carboxylic acid amide is an amino acid amide.

4. A method of making an enantiomerically enriched organic compound, comprising contacting enantiomerically mixed organic compounds with the isolated polypeptide of claim 1.

5. The method of claim 4, wherein the organic compound is an amino acid.

6. The method of claim 5, wherein the enantiomerically enriched amino acid is a D-amino acid.

7. An isolated polypeptide, which is at least 95% identical to a polypeptide comprising SEQ ID NO:2 and which has amidase activity.

8. A method of making a carboxylic acid, comprising contacting a carboxylic acid amide with the isolated polypeptide of claim 7.

9. The method of claim 8, wherein the carboxylic acid is an amino acid and the carboxylic acid amide is an amino acid amide.

10. A method of making an enantiomerically enriched organic compound, comprising contacting enantiomerically mixed organic compounds with the isolated polypeptide of claim 7.

11. The method of claim 10, wherein the organic compound is an amino acid.

12. The method of claim 11, wherein the enantiomerically enriched amino acid is a D-amino acid.

* * * * *

UNITED STATES PATENT AND TRADEMARK OFFICE
CERTIFICATE OF CORRECTION

PATENT NO. : 7,070,963 B2  Page 1 of 1
APPLICATION NO. : 10/309294
DATED : July 4, 2006
INVENTOR(S) : Verseck et al.

It is certified that error appears in the above-identified patent and that said Letters Patent is hereby corrected as shown below:

On the title page, Item (75), the 7th inventor's city of residence is incorrect. Item (75) should read:

-- (75) Inventors: Stefan Verseck, Hanau (DE); Karlheinz Drauz, Freigericht (DE); Andreas Bommarius, Atlanta, GA (US); Maria-Regina Kula, Niederzier (DE); Lutz Krieg, Juelich (DE); Heike Slusarczyk, Uebach-Palenberg (DE); Marion Ansorge-Schumacher, Roetgen (DE) --

Signed and Sealed this

Nineteenth Day of September, 2006

JON W. DUDAS
*Director of the United States Patent and Trademark Office*

SEQUENCE LISTING

```
<160> NUMBER OF SEQ ID NOS: 13

<210> SEQ ID NO 1
<211> LENGTH: 1398
<212> TYPE: DNA
<213> ORGANISM: Variovorax paradoxus
<220> FEATURE:
<221> NAME/KEY: CDS
<222> LOCATION: (1)..(1398)
<223> OTHER INFORMATION:

<400> SEQUENCE: 1 atg agc aac gaa ctg cat tac ctc gag ctg gtc gac gtc ggc cgg cgc      48
Met Ser Asn Glu Leu His Tyr Leu Glu Leu Val Asp Val Gly Arg Arg
1               5                  10                  15 atc cag cgc aag gag ctc tcg ccg gtc gag gtc acg caa gcg cag ctc      96
Ile Gln Arg Lys Glu Leu Ser Pro Val Glu Val Thr Gln Ala Gln Leu
            20                  25                  30 gcg cgc atc gag aag gtc gac ggc gcg ctc aag agc tat gtg atc gtg     144
Ala Arg Ile Glu Lys Val Asp Gly Ala Leu Lys Ser Tyr Val Ile Val
        35                  40                  45 atg gcc gaa cac gcg ctg gcc gac gcg cgc cgc gcc gag gcc gag atc     192
Met Ala Glu His Ala Leu Ala Asp Ala Arg Arg Ala Glu Ala Glu Ile
    50                  55                  60 gcc cgg ggc gag atc cgc ggg ccg ctg cac ggc gtg ccg gtg gcg gtg     240
Ala Arg Gly Glu Ile Arg Gly Pro Leu His Gly Val Pro Val Ala Val
65                  70                  75                  80 aag gac ctg tgc tgg aca aaa ggc gtg gcc acg gcc gcc ggc atg acg     288
Lys Asp Leu Cys Trp Thr Lys Gly Val Ala Thr Ala Ala Gly Met Thr
                85                  90                  95 ctc tac cgc gac ttc gtg ccc acc gag gac ggc acg gcc gtg cgc aag     336
Leu Tyr Arg Asp Phe Val Pro Thr Glu Asp Gly Thr Ala Val Arg Lys
            100                 105                 110 ctg cgc gaa gcc ggt gcc gtg atc ctc ggc aag ctg cag ctc acc gag     384
Leu Arg Glu Ala Gly Ala Val Ile Leu Gly Lys Leu Gln Leu Thr Glu
        115                 120                 125 agc gcc tat gcc gac cat cac ccc agc gtc acg ccg ccg gtc aat ccg     432
Ser Ala Tyr Ala Asp His His Pro Ser Val Thr Pro Pro Val Asn Pro
    130                 135                 140 tgg aac gcg gcg cac tgg tcg ggt gcc tcg tcg agc ggc tcg ggc gtg     480
Trp Asn Ala Ala His Trp Ser Gly Ala Ser Ser Ser Gly Ser Gly Val
145                 150                 155                 160 gcg acc gcg gcg ggg ctt tgc tat ggc tcg ctc ggc acc gac acg ggc     528
```

-continued

```
                Ala Thr Ala Ala Gly Leu Cys Tyr Gly Ser Leu Gly Thr Asp Thr Gly
                            165                 170                 175 ggc tcg atc cgc ttt ccg tcc tcg gcc aac ggc ctg acc ggc ctg aag         576
Gly Ser Ile Arg Phe Pro Ser Ser Ala Asn Gly Leu Thr Gly Leu Lys
            180                 185                 190 ccg acc tgg ggc cgc gtg agc cgc cat ggc gcc ttc gag ctg gcc gcc         624
Pro Thr Trp Gly Arg Val Ser Arg His Gly Ala Phe Glu Leu Ala Ala
        195                 200                 205 acg ctc gac cac atc ggc ccg atg acg cgc agc gcg gcc gat gcg ggt         672
Thr Leu Asp His Ile Gly Pro Met Thr Arg Ser Ala Ala Asp Ala Gly
    210                 215                 220 gcg atg ctc ggc gcc atc gcg gga gcc gat ccg aag gac ccg acc gcg         720
Ala Met Leu Gly Ala Ile Ala Gly Ala Asp Pro Lys Asp Pro Thr Ala
225                 230                 235                 240 agc ctc gcg gcc gtg ccc aac tac ctc gcg ggc atg gag cgc ggc ttg         768
Ser Leu Ala Ala Val Pro Asn Tyr Leu Ala Gly Met Glu Arg Gly Leu
                245                 250                 255 cgc ggc ctg cgc gtg ggc atc gac gcg cgc tgg aac gcg gag ggc gtc         816
Arg Gly Leu Arg Val Gly Ile Asp Ala Arg Trp Asn Ala Glu Gly Val
            260                 265                 270 gat gcg gcc acc gcg cag gtg atg gaa ggc gcg ctc gcg gcc gtg cgc         864
Asp Ala Ala Thr Ala Gln Val Met Glu Gly Ala Leu Ala Ala Val Arg
        275                 280                 285 gaa ctc ggc gcc gaa gtg cgt cac gtg aca ttc ccc gac ccg gcg cag         912
Glu Leu Gly Ala Glu Val Arg His Val Thr Phe Pro Asp Pro Ala Gln
    290                 295                 300 gtc atc gcc gac tgg ttc ccg ctg tgc ggc atc gag gcg gcc gtg gtg         960
Val Ile Ala Asp Trp Phe Pro Leu Cys Gly Ile Glu Ala Ala Val Val
305                 310                 315                 320 cac gag tcg acc tat ccc gcg cgc aag cag atg tac ggc ccg gcg ctg        1008
His Glu Ser Thr Tyr Pro Ala Arg Lys Gln Met Tyr Gly Pro Ala Leu
                325                 330                 335 tcg ggc ctg ctc gag ctg ggc cgt gcg caa agc ggc atc gac tac cag        1056
Ser Gly Leu Leu Glu Leu Gly Arg Ala Gln Ser Gly Ile Asp Tyr Gln
            340                 345                 350 aag atc gtg ctc cgc cgc cat gcc ttc agc ggc agg gtg cgc gag atg        1104
Lys Ile Val Leu Arg Arg His Ala Phe Ser Gly Arg Val Arg Glu Met
        355                 360                 365 ttc gag ggc atc gac ctg ctg ctg atg ccc tcg cag ggc gtc gcc tcg        1152
Phe Glu Gly Ile Asp Leu Leu Leu Met Pro Ser Gln Gly Val Ala Ser
    370                 375                 380 ccc acg ctc gcg cgc atg ctg agc ttc ggc gag gac gcc gaa ctg atg        1200
Pro Thr Leu Ala Arg Met Leu Ser Phe Gly Glu Asp Ala Glu Leu Met
385                 390                 395                 400 tcc gcg atg ctg cgc tac acc tgc ccg ctg gac atg agc ggc agc ccg        1248
Ser Ala Met Leu Arg Tyr Thr Cys Pro Leu Asp Met Ser Gly Ser Pro
                405                 410                 415 acg atc acg ctg ccc ggc ggc ttc acc gat gcg ggc acg ccg gtc gca        1296
Thr Ile Thr Leu Pro Gly Gly Phe Thr Asp Ala Gly Thr Pro Val Ala
            420                 425                 430 ttc cag ttc gtc gcg cgc cac ttc gag gaa gag ctg ctg gtg cgc gcc        1344
Phe Gln Phe Val Ala Arg His Phe Glu Glu Glu Leu Leu Val Arg Ala
        435                 440                 445 ggc tgg gcc ttc cag cag gcg acc gac tgg cac cgg cgg cat ccg gtg        1392
Gly Trp Ala Phe Gln Gln Ala Thr Asp Trp His Arg Arg His Pro Val
    450                 455                 460 ctg tag                                                                 1398
Leu
465
```

```
<210> SEQ ID NO 2
<211> LENGTH: 465
<212> TYPE: PRT
<213> ORGANISM: Variovorax paradoxus

<400> SEQUENCE: 2

Met Ser Asn Glu Leu His Tyr Leu Glu Leu Val Asp Val Gly Arg Arg
1               5                   10                  15

Ile Gln Arg Lys Glu Leu Ser Pro Val Glu Val Thr Gln Ala Gln Leu
                20                  25                  30

Ala Arg Ile Glu Lys Val Asp Gly Ala Leu Lys Ser Tyr Val Ile Val
            35                  40                  45

Met Ala Glu His Ala Leu Ala Asp Ala Arg Arg Ala Glu Ala Glu Ile
50                  55                  60

Ala Arg Gly Glu Ile Arg Gly Pro Leu His Gly Val Pro Val Ala Val
65                  70                  75                  80

Lys Asp Leu Cys Trp Thr Lys Gly Val Ala Thr Ala Ala Gly Met Thr
                85                  90                  95

Leu Tyr Arg Asp Phe Val Pro Thr Glu Asp Gly Thr Ala Val Arg Lys
                100                 105                 110

Leu Arg Glu Ala Gly Ala Val Ile Leu Gly Lys Leu Gln Leu Thr Glu
            115                 120                 125

Ser Ala Tyr Ala Asp His His Pro Ser Val Thr Pro Pro Val Asn Pro
130                 135                 140

Trp Asn Ala Ala His Trp Ser Gly Ala Ser Ser Gly Ser Gly Val
145                 150                 155                 160

Ala Thr Ala Ala Gly Leu Cys Tyr Gly Ser Leu Gly Thr Asp Thr Gly
                165                 170                 175

Gly Ser Ile Arg Phe Pro Ser Ser Ala Asn Gly Leu Thr Gly Leu Lys
                180                 185                 190

Pro Thr Trp Gly Arg Val Ser Arg His Gly Ala Phe Glu Leu Ala Ala
            195                 200                 205

Thr Leu Asp His Ile Gly Pro Met Thr Arg Ser Ala Ala Asp Ala Gly
210                 215                 220

Ala Met Leu Gly Ala Ile Ala Gly Ala Asp Pro Lys Asp Pro Thr Ala
225                 230                 235                 240

Ser Leu Ala Ala Val Pro Asn Tyr Leu Ala Gly Met Glu Arg Gly Leu
                245                 250                 255

Arg Gly Leu Arg Val Gly Ile Asp Ala Arg Trp Asn Ala Glu Gly Val
                260                 265                 270

Asp Ala Ala Thr Ala Gln Val Met Glu Gly Ala Leu Ala Ala Val Arg
            275                 280                 285

Glu Leu Gly Ala Glu Val Arg His Val Thr Phe Pro Asp Pro Ala Gln
290                 295                 300

Val Ile Ala Asp Trp Phe Pro Leu Cys Gly Ile Glu Ala Ala Val Val
305                 310                 315                 320

His Glu Ser Thr Tyr Pro Ala Arg Lys Gln Met Tyr Gly Pro Ala Leu
                325                 330                 335

Ser Gly Leu Leu Glu Leu Gly Arg Ala Gln Ser Gly Ile Asp Tyr Gln
                340                 345                 350

Lys Ile Val Leu Arg Arg His Ala Phe Ser Gly Arg Val Arg Glu Met
            355                 360                 365

Phe Glu Gly Ile Asp Leu Leu Leu Met Pro Ser Gln Gly Val Ala Ser
370                 375                 380
```

```
Pro Thr Leu Ala Arg Met Leu Ser Phe Gly Glu Asp Ala Glu Leu Met
385                 390                 395                 400

Ser Ala Met Leu Arg Tyr Thr Cys Pro Leu Asp Met Ser Gly Ser Pro
            405                 410                 415

Thr Ile Thr Leu Pro Gly Gly Phe Thr Asp Ala Gly Thr Pro Val Ala
                420                 425                 430

Phe Gln Phe Val Ala Arg His Phe Glu Glu Leu Leu Val Arg Ala
        435                 440                 445

Gly Trp Ala Phe Gln Gln Ala Thr Asp Trp His Arg Arg His Pro Val
    450                 455                 460

Leu
465

<210> SEQ ID NO 3
<211> LENGTH: 26
<212> TYPE: DNA
<213> ORGANISM: Artificial Sequence
<220> FEATURE:
<223> OTHER INFORMATION: synthetic DNA

<400> SEQUENCE: 3
gtsggccgsc gsatccagca gaagga                                    26

<210> SEQ ID NO 4
<211> LENGTH: 26
<212> TYPE: DNA
<213> ORGANISM: Artificial Sequence
<220> FEATURE:
<223> OTHER INFORMATION: synthetic DNA

<400> SEQUENCE: 4
gggatscgga tcgagccgcc sgtstc                                    26

<210> SEQ ID NO 5
<211> LENGTH: 509
<212> TYPE: DNA
<213> ORGANISM: Artificial Sequence
<220> FEATURE:
<223> OTHER INFORMATION: synthetic DNA

<400> SEQUENCE: 5
gtcggccggc gcatccagcg caaggagctc tcgccggtcg aggtcacgca agcgcagctc    60
gcgcgcatcg agaaggtcga cggcgcgctc aagagctatg tgatcgtgat ggccgaacac   120
gcgctggccg acgcgcgccg cgccgaggcc gagatcgccc ggggcgagat ccgcgggccg   180
ctgcacggcg tgccggtggc ggtgaaggac ctgtgctgga caaaaggcgt ggccacggcc   240
gccggcatga cgctctaccg cgacttcgtg cccaccgagg acggcacggc cgtgcgcaag   300
ctgcgcgaag ccggtgccgt gatcctcggc aagctgcagc tcaccgagag cgcctatgcc   360
gaccatcacc ccagcgtcac gccgccggtc aatccgtgga cgcggcgca ctggtcgggt   420 gcctcgtcga gcggctcggg cgtggcgacc gcggcggggc tttgctatgg ctcgctcggc   480
accgacacgg gcggctcgat ccgctttcc                                    509

<210> SEQ ID NO 6
<211> LENGTH: 28
<212> TYPE: DNA
<213> ORGANISM: Artificial Sequence
<220> FEATURE:
<223> OTHER INFORMATION: synthetic DNA
```

<400> SEQUENCE: 6
gcgtcacgcc gccggtcaat ccgtggaa                                28

<210> SEQ ID NO 7
<211> LENGTH: 26
<212> TYPE: DNA
<213> ORGANISM: Artificial Sequence
<220> FEATURE:
<223> OTHER INFORMATION: synthetic DNA

<400> SEQUENCE: 7
ggcgcactgg tcgggtgcct cgtcga                                  26

<210> SEQ ID NO 8
<211> LENGTH: 30
<212> TYPE: DNA
<213> ORGANISM: Artificial Sequence
<220> FEATURE:
<223> OTHER INFORMATION: synthetic DNA

<400> SEQUENCE: 8
cagcgcgtgt tcggccatca cgatcacata                              30

<210> SEQ ID NO 9
<211> LENGTH: 28
<212> TYPE: DNA
<213> ORGANISM: Artificial Sequence
<220> FEATURE:
<223> OTHER INFORMATION: synthetic DNA

<400> SEQUENCE: 9
ctcttgagcg cgccgtcgac cttctcga                                28

<210> SEQ ID NO 10
<211> LENGTH: 27
<212> TYPE: DNA
<213> ORGANISM: Artificial Sequence
<220> FEATURE:
<223> OTHER INFORMATION: synthetic DNA

<400> SEQUENCE: 10
ctggtcatca agcgcggcca gatcggc                                 27

<210> SEQ ID NO 11
<211> LENGTH: 26
<212> TYPE: DNA
<213> ORGANISM: Artificial Sequence
<220> FEATURE:
<223> OTHER INFORMATION: synthetic DNA

<400> SEQUENCE: 11
gatcggccga cagccgattg gccagc                                  26

<210> SEQ ID NO 12
<211> LENGTH: 32
<212> TYPE: DNA
<213> ORGANISM: Artificial Sequence
<220> FEATURE:
<223> OTHER INFORMATION: synthetic DNA

<400> SEQUENCE: 12
ccggaattca tgagcaacga actgcattac ct                           32

<210> SEQ ID NO 13
<211> LENGTH: 29

```
-continued
<212> TYPE: DNA
<213> ORGANISM: Artificial Sequence
<220> FEATURE:
<223> OTHER INFORMATION: synthetic DNA

<400> SEQUENCE: 13
atcccaagct tttacagcac cggatgccg                                   29
```